(12) United States Patent
Kweon et al.

(10) Patent No.: US 8,500,808 B2
(45) Date of Patent: Aug. 6, 2013

(54) ARTIFICIAL EARDRUM USING SILK PROTEIN AND METHOD OF FABRICATING THE SAME

(75) Inventors: Hae Yong Kweon, Suwon-Si (KR); Kwang Gill Lee, Suwon-Si (KR); Seok Woo Kang, Hwaseong-Si (KR); Joo Hong Yeo, Suwon-Si (KR); You Young Jo, Yongin-Si (KR); Soon Ok Woo, Suwon-Si (KR); Sang-Mi Han, Seosan-Si (KR); Chan Hum Park, Chuncheon-Si (KR); Jin Kim, Seoul (KR); Chun Hwoi Kim, Namyangju-Si (KR)

(73) Assignees: Republic of Korea represented by Rural Development Administration (KR); Industry Academic Cooperation Foundation, Hallym University (KR)

( * ) Notice: Subject to any disclaimer, the term of this patent is extended or adjusted under 35 U.S.C. 154(b) by 375 days.

(21) Appl. No.: 12/493,277

(22) Filed: Jun. 29, 2009

(65) Prior Publication Data

US 2010/0286774 A1    Nov. 11, 2010

(30) Foreign Application Priority Data

May 8, 2009 (KR) .................. 10-2009-0040200

(51) Int. Cl.
*A61F 2/18* (2006.01)
(52) U.S. Cl.
USPC ........................................................ 623/10
(58) Field of Classification Search
None
See application file for complete search history.

(56) References Cited

U.S. PATENT DOCUMENTS

| 6,110,590 A | 8/2000 | Zarkoob et al. | |
|---|---|---|---|
| 2006/0095137 A1* | 5/2006 | Chung et al. | 623/23.58 |

FOREIGN PATENT DOCUMENTS

| CN | 1483866 A | 3/2004 |
|---|---|---|
| CN | 1904159 A | 1/2007 |
| CN | 101234213 A | 8/2008 |
| JP | 6485272 | 3/1989 |
| JP | 6508363 | 9/1994 |
| KR | 1020000051938 | 8/2000 |
| KR | 1020000068154 | 11/2000 |
| KR | 1020010052075 | 6/2001 |
| KR | 1020030097691 | 12/2003 |

(Continued)

OTHER PUBLICATIONS

Ghassemifar, et al, "Advancing Towards a Tissue-Engineered Tympanic Membrane: Silk Fibroin as a Substratum for Growing Human Eardrum Keratinocytes", Journal of Biomaterials Applications, Apr. 22, 2009.*

(Continued)

*Primary Examiner* — David Isabella
*Assistant Examiner* — Leslie Coburn
(74) *Attorney, Agent, or Firm* — Schmeiser, Olsen & Watts LLP

(57) ABSTRACT

Provided is an artificial eardrum using silk protein and a method of fabricating the same. The artificial eardrum is fabricated in the form of a silk membrane by desalinating and drying silk protein (or silk fibroin) or a silk protein complex solution obtained after removal of sericin from a silkworm cocoon or silk fiber. Thus, regeneration of an eardrum perforated due to disease or a sudden accident is stimulated, a boundary of the regenerated eardrum is clean and biocompatibility and transparency are increased. In addition, the artificial eardrum may be fabricated using the silk protein or silk protein complex solution obtained from a silkworm cocoon alone or mixed with collagen, alginic acid, PEG or pluronic 127.

6 Claims, 5 Drawing Sheets

FOREIGN PATENT DOCUMENTS

| KR | 1020040011786 | | 2/2004 |
|---|---|---|---|
| KR | 1020040011786 | * | 11/2004 |
| KR | 2008040516 | * | 5/2008 |
| KR | 1020060108573 | | 5/2008 |
| WO | 03022909 A1 | | 3/2003 |

OTHER PUBLICATIONS

She, et al "Silk fibroin/chitosan scaffold: preparation, characterization, and culture with HepG2 cell", J Mat Sci, 2008, v. 19, pp. 3545-3553.*

Altman, et al "Silk-based Biomaterials", Biomaterials, v. 24 (2003), pp. 401-406.*

Jin, Hyoung-Joon, et al, "Biomaterial Films of Bombyx Mori Silk Fibroin with Poly(ethylene oxide)", Biomacromolecules, 2004, v5, pp. 711-717.*

Chinese Patent Application No. JP200910150124.7, Office Action dated Mar. 30, 2012. 13 pages.

Chen, Guogiang, 'Study of Silk Solubility and Regenerated Membrane Structure'. Journal of Suzhou Institute of Silk Textile Technology, Issue 2, pp. 45-52, Apr. 30, 1986. (Abstract) CNKI [online] [retrieved on Jul. 26, 2012]. Retrieved from: CNKI, :< URL:http://en.cnki.com.cn/Article_en/CJFDTOTAL-SILK198602004.htm>.

Ghassemifar, Reza et al. 'Advancing Towards a Tissue-Engineered Tympanic Membrane: Silk Fibroin as a Substratum for Growing Human Eardrum Keratinocytes', Journal of Biomaterials Appplications, Apr. 22, 2009, DOI: 10.1177/0885328209104289. SAGE [online]. UK [retrieved on Mar. 6, 2012]. Retrieved from: Sage Publications: <URL: http::jba.sagepub.com/content/early/2009/04/22/0885328209104289.

Japanese Patent Application No. JP2009-154428, Office Action dated Mar. 14, 2012. 11 pages.

Japanese Patent Application No. JP2009154428, Office Action dated Jul. 4, 2012. 4 pages.

Jin, Hyoung-Joon, et al. 'Biomaterial Films of Bombyx Mori Silk Fibroin with Poly(ethylene oxidey)'. Biomacromolecules, 2004, vol. 5, pp. 711-717. 8 pages.

She, Zhending, et al. 'Silk fibroin/chitosan scaffold: preparation, characterization, and culture with HepG2 cell', J. Mater Sci: Mater. Med., 2008, vol. 19, pp. 3545-3553. 10 pages.

European Patent Application No. EP 09 164 040.9, Office Action dated Jun. 15, 2012. 4 pages.

* cited by examiner

ARTIFICIAL EARDRUM USING SILK PROTEIN AND METHOD OF FABRICATING THE SAME

CROSS-REFERENCE TO RELATED APPLICATION

This application claims the benefit of Korean Patent Application No. 2009-0040200, filed on May 8, 2009, the disclosure of which is hereby incorporated herein by reference in its entirety.

BACKGROUND OF THE INVENTION

1. Field of the Invention

The present invention relates to an artificial eardrum using silk protein and a method of fabricating the same, and more particularly, to an artificial eardrum using silk protein having a form of a silk membrane using silk protein or a complex thereof obtained by removing sericin from a silkworm cocoon as a material for the artificial eardrum, which stimulates regeneration of an eardrum perforated due to disease or a sudden accident, provides a clean boundary of the regenerated eardrum, and is easy to use due to high biocompatibility and transparency, and a method of fabricating the same.

2. Description of the Related Art

Generally, silk is a fabric made from silkworm cocoons spun by silkworms raised on mulberry leaves, and has been used as a material for high quality fabric for several thousand years due to its unique shine, good dyeing property, high tensile strength, smooth texture and elegant sound when brushed against.

The silk is composed of two strands of fibroin and sericin surrounding the fibroin, and generally refers to the fibroin that remains after removal of the sericin. Since silk fibroin has no bad influence upon tissues existing therearound due to high biocompatibility, it is manufactured in powders, gels and aqueous solutions and thus applied to various fields such as foods, cosmetics and the like.

In addition, silk fibroin is known to have effects in proliferation and activation of epidermal cells originating from human bodies, and thus has been discussed with regard to use for cosmetic materials (Korean Patent Publication No. 2001-52075), wound dressing (Korean Patent Publication Nos. 1999-7001234 and 2000-51938), and electrospinning nanofiber non-woven fabrics (Korean Patent Publication No. 2004-0011786, and U.S. Pat. No. 6,110,590). However, no silk materials for an artificial eardrum have been disclosed.

Meanwhile, conventional myringoplasty and patches stimulate regeneration of an eardrum perforated due to trauma or inflammation. Particularly, the myringoplasty helps an epithelium of an eardrum to grow at a perforated site using autogenous fascia or other soft tissues.

However, to harvest autogenous fascia and soft tissues, a donor harvesting operation is needed, which may cause inflammations and scars, and an increase in operation time.

An eardrum patch induces regeneration of a planar epithelium layer along the patch by applying the patch to completely contact a perforated peripheral portion of the eardrum, and thus increases a therapeutic success for a short period of time without complications. This method has been frequently used for treating traumatic eardrum perforation since it was suggested by Blake in 1887.

This method does not involve replacing the perforated eardrum with an artificial eardrum, but naturally helping to block the perforated eardrum by applying a patch to the perforated site of the eardrum. The regenerated eardrum is grown along the patch-applied site.

However, conventional materials for an eardrum patch are usually paper patches, which are not very efficient or compatible due to long regeneration time and a thickness of the regenerated eardrum.

If the perforated eardrum is left for a long period of time, chronic tympanitis may occur. It is known that a paper patch is generally used to treat the chronic eardrum perforation, but it can cause inflammation. Moreover, it is expected that it will not be easy to regenerate the perforated eardrum as senior population is increased due to aging society, and thus it is urgent to develop and market novel products for artificial eardrums.

SUMMARY OF THE INVENTION

The present invention is directed to an artificial eardrum using silk protein having a form of a silk membrane using silk protein or a complex thereof obtained by removing sericin from a silkworm cocoon as a material for the artificial eardrum, which stimulates regeneration of an eardrum perforated due to disease or a sudden accident, provides a clean boundary of the regenerated eardrum, and is easy to use due to high biocompatibility and transparency, and a method of fabricating the same.

According to an aspect of the present invention, there is provided an artificial eardrum using silk protein which is fabricated into a silk membrane by desalinating and drying silk protein or a complex solution thereof which is obtained after removal of sericin from a cocoon or fibroin.

Here, the silk membrane may be fabricated using silk protein or a silk protein complex solution with a concentration of 0.8 to 20% at room temperature to 90° C.

The silk protein or silk protein complex solution may be dissolved using a chaotropic salt composed of at least one compound or an ethanol aqueous solution including the same selected from lithium bromide (LiBr), lithium chloride (LiCl$_2$), zinc chloride (ZnCl$_2$) and calcium chloride (CaCl$_2$).

The silk membrane may further include at least one additive selected from gelatin, collagen, chitosan, alginic acid, hyarulonic acid, pluronic 127 and poly(ethylene glycol) (PEG).

The silk membrane may further include at least one additive selected from a plasticizer, a softener, an antibiotic, an antibacterial agent, a cell, an enzyme, an antibody and a pigment or a combination thereof to prevent additional infection at a silk membrane-applied site.

According to another aspect of the present invention, a method of fabricating an artificial eardrum using silk protein includes: (a) preparing silk protein or a silk protein complex solution after removal of sericin from a cocoon or fibroin; and (b) desalinating and drying the prepared silk protein or silk protein complex solution to fabricate the prepared silk protein or silk protein complex solution into a silk membrane.

Here, after step (a), the silk protein or silk protein complex solution may be dissolved using a chaotropic salt composed of at least one compound selected from lithium bromide (LiBr), lithium chloride (LiCl$_2$), zinc chloride (ZnCl$_2$) and calcium chloride (CaCl$_2$) or an ethanol aqueous solution including the same.

After step (b), the silk membrane may be recrystallized by heat treatment or solvent treatment to reduce solubility to water.

The solvent may be at least one alcohol of methanol, ethanol and propanol or an aqueous solution thereof.

A concentration of the silk protein or silk protein complex solution prepared in step (a) may be controlled using PEG or by drying under reduced pressure using a drier or vacuum drier.

The silk membrane fabricated in step (b) may include at least one additive of gelatin, collagen, chitosan, alginic acid, hyarulonic acid, pluronic 127 and PEG.

BRIEF DESCRIPTION OF THE DRAWINGS

These and/or other objects, aspects and advantages of the invention will become apparent and more readily appreciated from the following description of the exemplary embodiments, taken in conjunction with the accompanying drawings of which.

DETAILED DESCRIPTION OF THE INVENTION

Reference will now be made in detail to exemplary embodiments of the present invention, examples of which are shown in the accompanying drawings. However, it should be understood that the present invention is not limited to the described exemplary embodiments, but includes various modifications, equivalents and alternatives. The exemplary embodiments of the present invention are provided to more fully explain the present invention to those skilled in the art.

To begin with, an artificial eardrum using silk protein of the present invention is an artificial biological membrane which is fabricated using a silk material and useful for acute and chronic eardrum perforations. The artificial eardrum may include artificial biological membranes using silk as well as patches for the eardrum.

Figure 1:
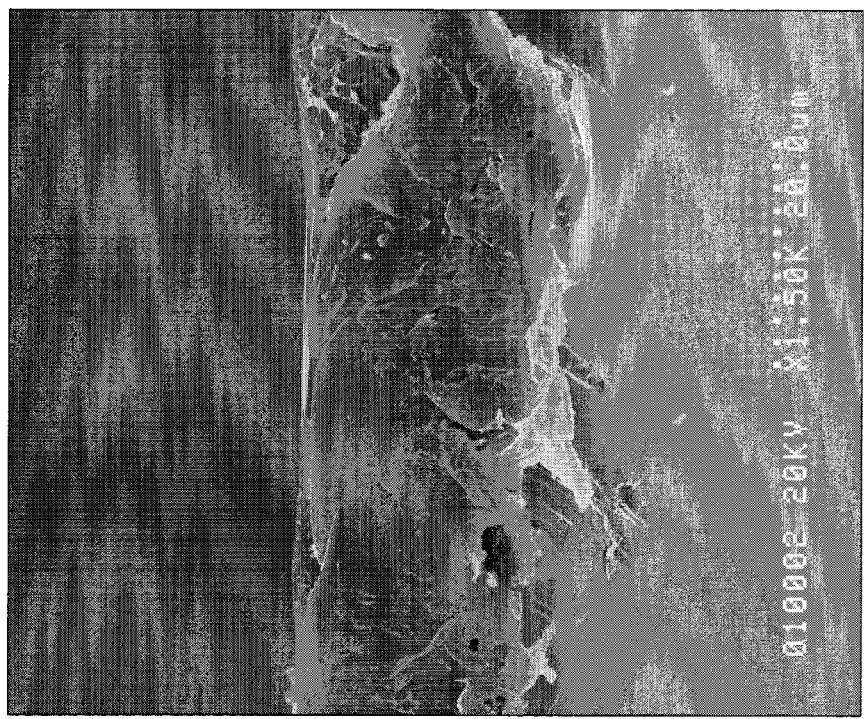
FIG. 1 is a silk membrane for an artificial eardrum using silk protein and a fractured surface thereof according to an exemplary embodiment of the present invention.
Figure 1:
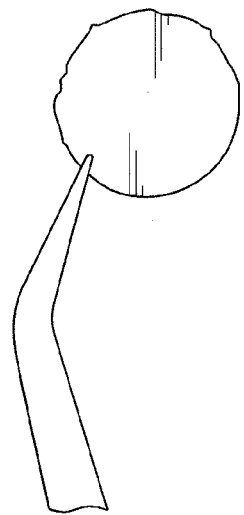
Figure 2:
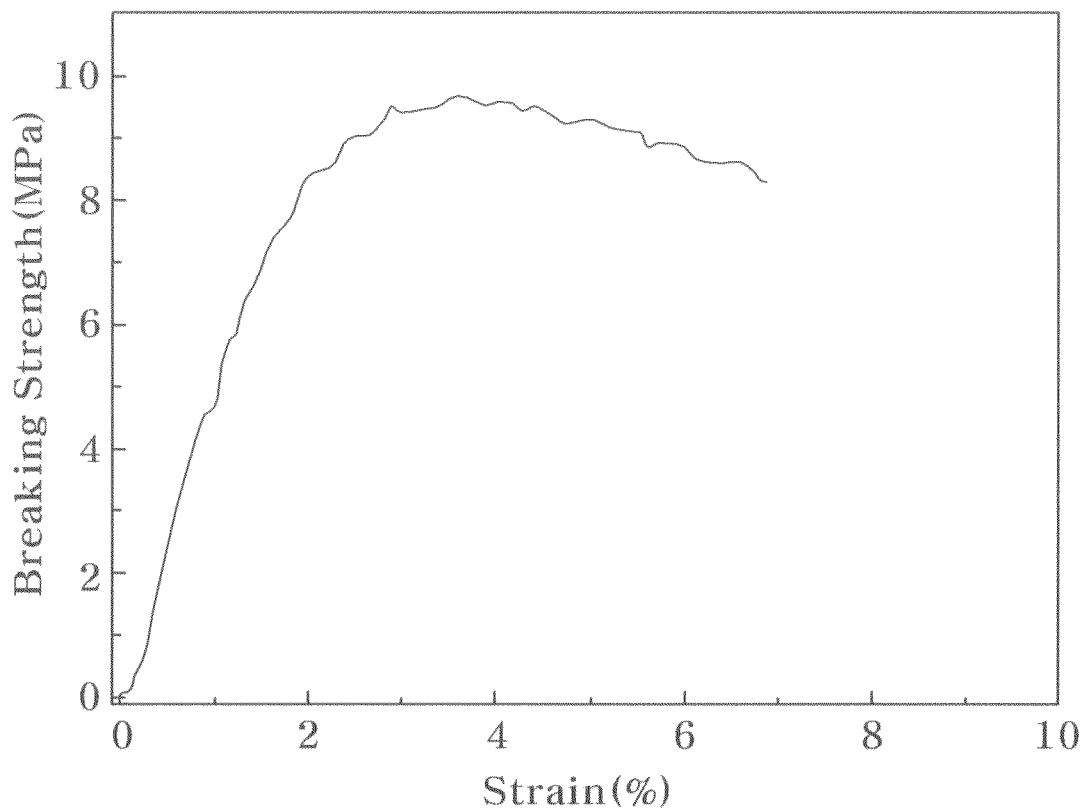
FIG. 2 is an exemplary tensile strength curve of a silk membrane for an artificial eardrum using silk protein according to an exemplary embodiment of the present invention.

FIG. 1 is a silk membrane for an artificial eardrum using silk protein and a fractured surface thereof according to an exemplary embodiment of the present invention, and FIG. 2 is an exemplary tensile strength curve of a silk membrane for an artificial eardrum using silk protein according to an exemplary embodiment of the present invention.

Referring to FIGS. 1 and 2, an artificial eardrum using silk protein according to an exemplary embodiment of the present invention is fabricated into a silk membrane using silk protein (or silk fibroin) or a silk protein complex obtained after removal of sericin from a cocoon or silk fiber.

Here, the silk membrane for an artificial eardrum may be fabricated to a thickness of about 30 to 200 μm by properly controlling a concentration of the silk protein and a membrane fabrication temperature. In consideration of contact with a perforated eardrum, a mechanical strength of an artificial eardrum and the like, a silk artificial eardrum may have a thickness of about 80 to 120 μm.

Particularly, the artificial eardrum of the present invention may effectively regenerate a damaged artificial eardrum due to its transparency, excellent cellular compatibility and biocompatibility, and prevention of invasion of bacteria from outside. Thus, even a damaged tissue may be effective in the regeneration of an eardrum. Moreover, according to an example of the present invention, the artificial eardrum fabricated using silk protein exhibits significant recovery of the artificial eardrum after 3 days of an operation.

The artificial eardrum of the present invention may further include at least one additive of gelatin, collagen, chitosan, alginic acid, hyarulonic acid, pluronic 127 and poly(ethylene glycol) (PEG) to be manageable in a dry state.

The artificial eardrum of the present invention may further include at least one additive selected from the group consisting of plasticizers, softeners, antibiotics, antibacterial agents, cells, enzymes, antibodies and pigments and combinations thereof.

Hereinafter, a method of fabricating an artificial eardrum using silk protein according to an exemplary embodiment of the present invention will be described in detail.

To begin with, an artificial eardrum using silk protein according to an exemplary embodiment of the present invention is a silk membrane fabricated using silk protein or a silk protein complex solution with a concentration of 0.8 to 20% obtained after removal of sericin from a cocoon or silk fiber at room temperature to 90° C.

Here, the silk membrane fabricated according to an exemplary embodiment of the present invention may be recrystallized to reduce solubility to water. The method used for recrystallization may be thermal treatment or solvent treatment. The solvent may include any of $C_1$ to $C_3$ alcohols such as methanol, ethanol and propanol, or an aqueous solution thereof.

Meanwhile, a process of removing sericin from a cocoon or raw silk refers to degumming. Such degumming processes are well known to those skilled in the art. For example, examples of the degumming processes include a method of boiling Marseille soap, sodium carbonate and the like in an alkali aqueous solution, a degumming method using a protease extracted from *Aspergillus* sp. and the like, and a high temperature high pressure method using a high temperature and high pressure pot. If a subsequent process is continued without the removal of sericin, many bubbles may be generated, which may cause considerable amounts of problems in processes.

The silk protein (or silk fibroin) from which sericin is removed is fabricated by being dissolved in a chaotropic salt that is known to dissolve protein. Neutral salts used in fabrication of the silk protein solution are also well known. For example, a degummed cocoon or fiber or fabrics is dissolved in an ethanol aqueous solution containing lithium bromide (LiBr), lithium chloride ($LiCl_2$), zinc chloride ($ZnCl_2$) or calcium chloride ($CaCl_2$), and then the resulting solution is dialyzed using a dialysis membrane such as cellophane, thereby completely removing the neutral salt.

The silk protein solution may properly control conditions dissolving the silk protein, a concentration and a dry temperature, thereby properly controlling a thickness of the silk membrane for the artificial eardrum in a range from about 30 to 200 μm.

In addition, to control the concentration of the silk protein or silk protein complex solution, PEG may be used or drying under reduced pressure may be performed using a dryer or vacuum dryer.

Further, the fabricated silk membrane may include at least one additive of gelatin, collagen, chitosan, alginic acid, hyarulonic acid, pluronic 127 and PEG.

Figure 3:
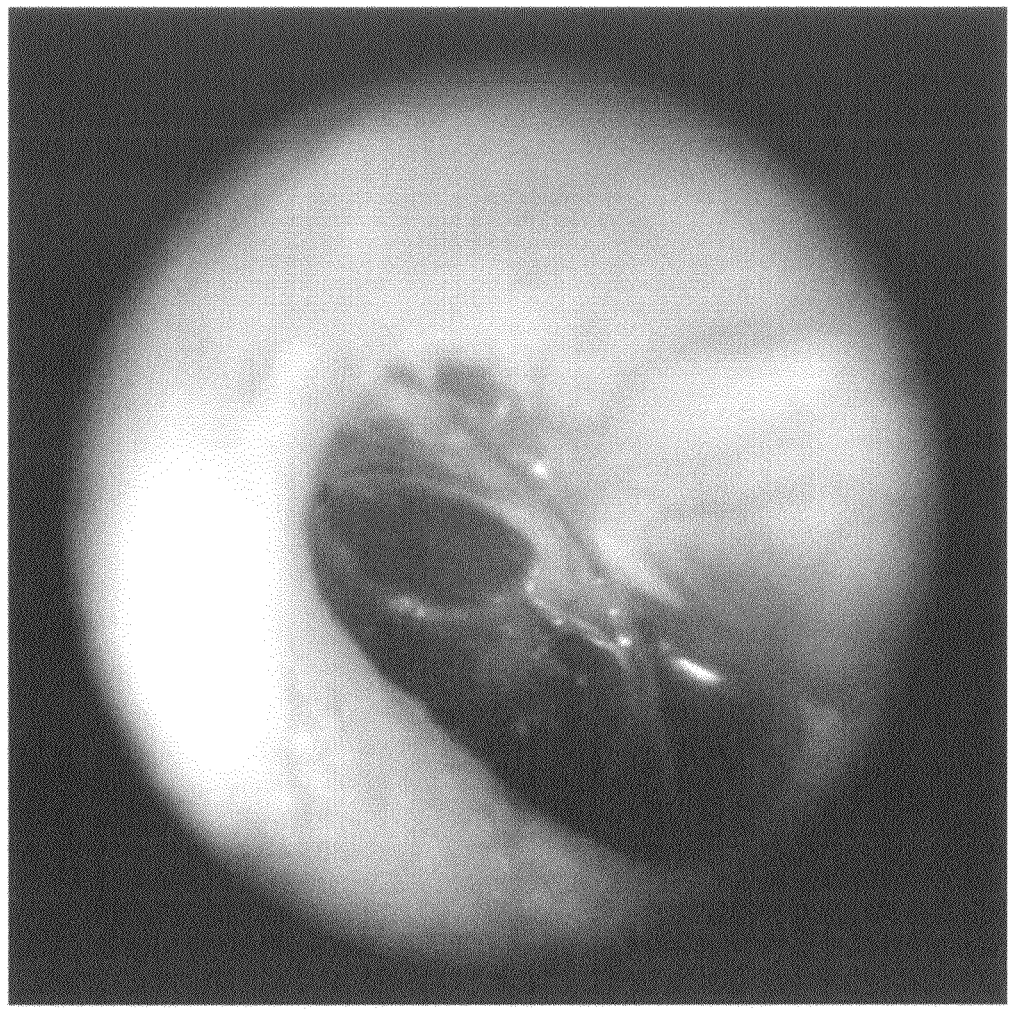
FIG. 3 is a photograph in which a membrane patch fabricated using silk protein of the present invention is applied to a perforated eardrum in an animal model.
Figure 4:
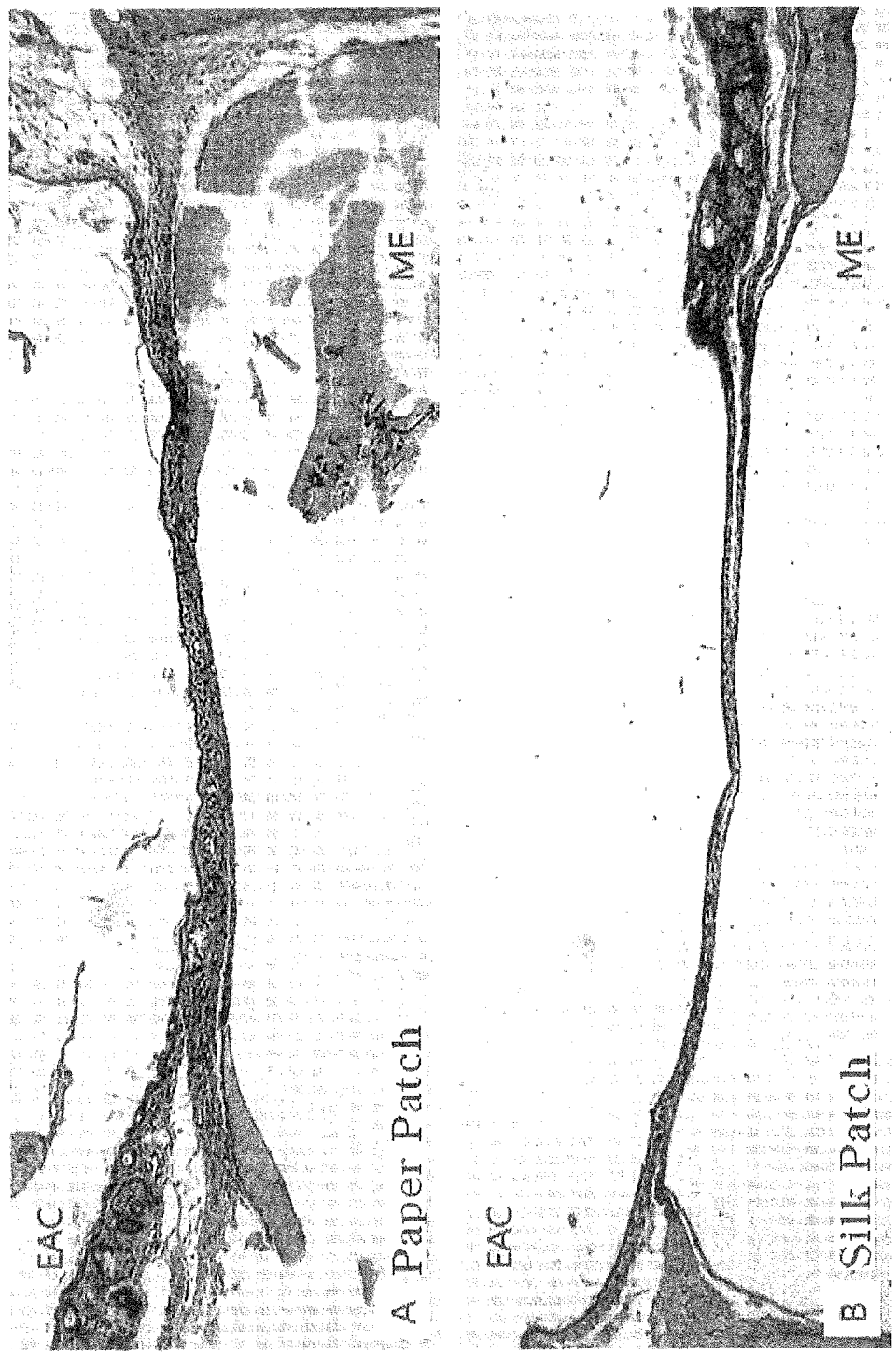
FIG. 4 is a histological result of the membrane fabricated using silk protein of the present invention, which is obtained from an animal having a perforated eardrum.
Figure 5:
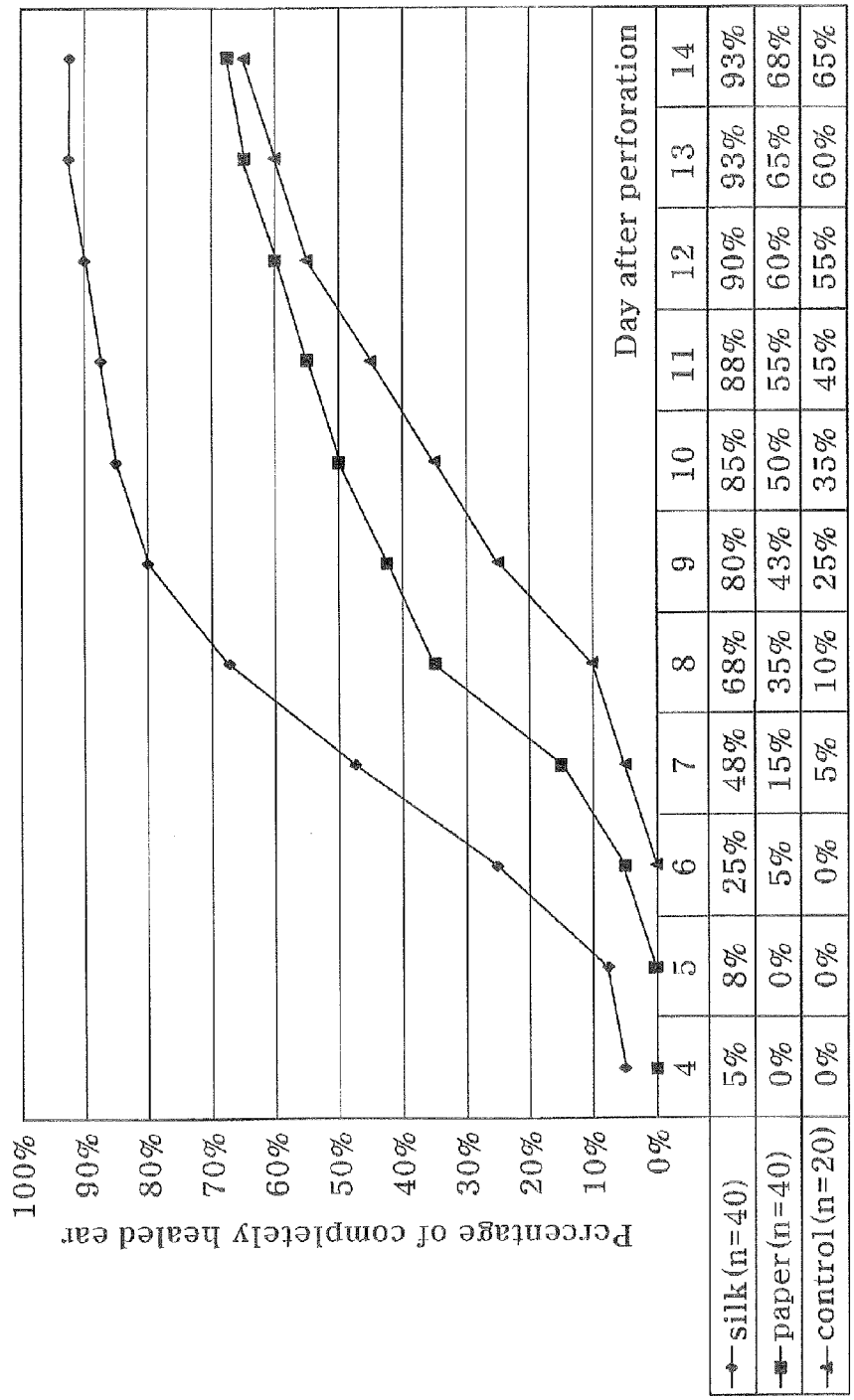
FIG. 5 is a graph and chart of a histological result of the membrane fabricated using silk protein of the present invention, which is obtained from an animal having a perforated eardrum.

FIG. 3 is a photograph in which a membrane patch fabricated using silk protein of the present invention is applied to a perforated eardrum in an animal model, FIG. 4 is a histological result of the membrane fabricated using silk protein of the present invention, which is obtained from an animal having a perforated eardrum, and FIG. 5 is a graph and chart of a histological result of a membrane fabricated using silk protein of the present invention, which is obtained from an animal having a perforated eardrum.

Referring to FIGS. 3 to 5, a silkworm cocoon is carefully selected after a contaminated portion, for example, by silkworm excretions, is removed, and then immersed in water having a weight 100 times that of the cocoon. The silkworm cocoon is treated with 0.2% Marseille soap and 0.2% sodium carbonate per material weight two times for about 50 minutes at the boiling point, and then washed with boiling water several times, thereby removing sericin.

The silkworm cocoon from which sericin is removed is placed in a mixed solvent including calcium chloride, water and ethanol in a molar ratio of 1:8:2 to dissolve at the boiling point for about 3 hours and centrifuged, thereby removing remaining impurities. To remove the salt from the dissolved silkworm cocoon solution, the solution is dialyzed for about 4 days using a cellulose dialysis membrane, thereby fabricating a pure silk protein solution.

The silk protein solution is dried at a constant temperature of about 60° C., thereby fabricating a silk membrane. When the fabricated silk membrane is observed by a scanning electron microscope as shown in FIG. 1, it can be confirmed that a nonporous, transparent and smooth silk membrane is fabricated.

Here, the mechanical strength of the silk membrane is obtained by measurements repeated at least about 10 times after conditioning for about 48 hours at a relative humidity of about 65% at room temperature, which are standard conditions. An average breaking strength of the silk membrane is about 10 MPa, and this is similar to about 12.5 MPa which is a breaking strength of a paper patch generally used.

In addition, to observe surface characteristics of the silk membrane, after about 5 seconds of dropping distilled water, a contact angle is measured using a contact angle measurer (Kruss easydrop), and is in a range from about 45 to 55°. Thus, the silk membrane is preferable for regeneration of an eardrum.

According to the aforementioned artificial eardrum and a method of fabricating the same of the present invention, the artificial eardrum is fabricated into a silk membrane by desalinating and drying silk protein or a silk protein complex solution obtained after removal of sericin from a silkworm cocoon or silk fiber. Thus, the artificial eardrum stimulates regeneration of an eardrum perforated due to disease or a sudden accident, thereby providing a clean boundary of the regenerated eardrum, and advantages of biocompatibility and transparency.

In addition, the present invention can reduce occurrence of donor harvesting operations which may be performed due to autograft, and thus not only avoid complications due to the donor harvesting operations, but also reduce complications compared with conventional artificial materials due to high biocompatibility.

According to the present invention, it is possible to massively produce eardrums and to fabricate the eardrums in various shapes.

Moreover, according to the present invention, short operation time and speedy post-surgical recovery can be provided to a patient, which are useful for both patients and doctors.

Although a few embodiments of the present invention have been shown and described, it would be appreciated by those skilled in the art that changes may be made in these embodiments without departing from the principles and spirit of the invention, the scope of which is defined in the claims and their equivalents.

What is claimed is:

1. An artificial eardrum comprising: a silk protein that is fabricated into a nonporous and transparent silk membrane by desalinating and drying silk protein or a silk protein complex solution obtained after removal of sericin from a silkworm cocoon or silk fiber, wherein the nonporous and transparent silk membrane is fashioned in the form of an artificial eardrum, and further includes at least one additive of gelatin, collagen, alginic acid, hyarulonic acid and pluronic 127, and has a thickness of 80-120 um, and is fabricated using the silk protein or the silk protein complex solution, which has a concentration of 0.8% to 20% at room temperature to 90° C., and the nonporous and transparent silk membrane is recrystallized using ethanol, propanol or an aqueous solution thereof.

2. The apparatus of claim 1, wherein the silk protein or the silk protein complex solution is dissolved using a chaotropic salt composed of at least one compound of lithium bromide (LiBr), lithium chloride ($LiCl_2$), zinc chloride ($ZnCl_2$) and calcium chloride ($CaCl_2$) or an ethanol aqueous solution including the same.

3. The apparatus of claim 1, wherein the nonporous and transparent silk membrane further includes at least one additive of a plasticizer, a softener, an antibiotic, an antibacterial agent, a cell, an enzyme, an antibody, a pigment and a combination thereof to prevent additional contamination of an applied site.

4. A method of fabricating an artificial eardrum, comprising:
   (a) preparing silk protein or a silk protein complex solution after removal of sericin from a silkworm cocoon or silk fiber;
   (b) desalinating and drying the prepared silk protein or silk protein complex solution to fabricate the prepared silk protein or silk protein complex solution into a nonporous and transparent silk membrane; and
   (c) fashioning the nonporous and transparent silk membrane to form the artificial eardrum,
   further comprising, after step (b), recrystallizing the nonporous and transparent silk membrane by solvent treatment using ethanol and propanol or an aqueous solution thereof to reduce solubility to water,
   wherein the nonporous and transparent silk membrane further includes at least one additive of gelatin, collagen, alginic acid, hyarulonic acid and pluronic 127 and has a thickness of 80-120 um, and the silk protein or the silk protein complex solution has a concentration of 0.8% to 20% at room temperature to 90° C.

5. The method of claim 4, further comprising, after step (a), dissolving the silk protein or the silk protein complex solution using a chaotropic salt composed of at least one compound of lithium bromide (LiBr), lithium chloride ($LiCl_2$), zinc chloride ($ZnCl_2$) and calcium chloride ($CaCl_2$) or an ethanol aqueous solution including the same.

6. The method of claim 4, wherein the concentration of the silk protein or the silk protein complex solution prepared in step (a) is controlled using poly(ethylene glycol)(PEG) or by drying under reduced pressure using a drier or vacuum drier.

* * * * *